United States Patent
Schlegl et al.

(10) Patent No.: US 10,679,344 B2
(45) Date of Patent: Jun. 9, 2020

(54) COMPUTERIZED DEVICE AND METHOD FOR PROCESSING IMAGE DATA

(71) Applicant: Medizinische Universität Wien, Vienna (AT)

(72) Inventors: Thomas Schlegl, Vienna (AT); Wolf-Dieter Vogl, Gänserndorf (AT); Georg Langs, Vienna (AT); Sebastian Waldstein, Vienna (AT); Bianca Gerendas, Vienna (AT); Ursula Schmidt-Erfurth, Vienna (AT)

( * ) Notice: Subject to any disclaimer, the term of this patent is extended or adjusted under 35 U.S.C. 154(b) by 0 days.

(21) Appl. No.: 15/554,414

(22) PCT Filed: Feb. 29, 2016

(86) PCT No.: PCT/EP2016/054249
§ 371 (c)(1),
(2) Date: Aug. 29, 2017

(87) PCT Pub. No.: WO2016/139183
PCT Pub. Date: Sep. 9, 2016

(65) Prior Publication Data
US 2018/0047159 A1    Feb. 15, 2018

(30) Foreign Application Priority Data

Mar. 2, 2015   (EP) ..................... 15157253

(51) Int. Cl.
*G06T 7/00* (2017.01)
*G06K 9/62* (2006.01)
(Continued)

(52) U.S. Cl.
CPC ............ *G06T 7/0012* (2013.01); *A61B 3/102* (2013.01); *G06F 17/15* (2013.01); *G06K 9/6267* (2013.01);
(Continued)

(58) Field of Classification Search
None
See application file for complete search history.

(56) References Cited

U.S. PATENT DOCUMENTS 8,879,813 B1 * 11/2014 Solanki ................. G06T 7/0014
382/128
9,430,706 B1 * 8/2016 Peleg ................. G06K 9/00765
(Continued)

FOREIGN PATENT DOCUMENTS

EP          3065086 A1      9/2016
WO     2008133951 A2     11/2008
WO     WO2008/133951    * 11/2008

OTHER PUBLICATIONS

Zheng, Yalin, et al. "Computerized assessment of intraretinal and subretinal fluid regions in spectral-domain optical coherence tomography images of the retina." American journal of ophthalmology 155.2 (2013): 277-286.*

(Continued)

*Primary Examiner* — Andrae S Allison
(74) *Attorney, Agent, or Firm* — Alleman Hall Creasman & Tuttle LLP (57) ABSTRACT

A computerized device for processing image data is proposed. The computerized device comprises a receiving unit which is configured to receive optical coherence tomography data of a of a tissue, in particular of a retina, a providing unit which is configured to provide a convolutional neural network for processing the optical coherence tomography data, and a processing unit which is configured to process the received optical coherence tomography data using the convolutional neural network for identifying at least one certain object in the tissue.

13 Claims, 7 Drawing Sheets

(51) Int. Cl.
*A61B 3/10* (2006.01)
*G06F 17/15* (2006.01)
*G06N 3/04* (2006.01)
*G06N 3/08* (2006.01)

(52) U.S. Cl.
CPC .......... *G06N 3/04* (2013.01); *G06N 3/08*
(2013.01); *G06T 2207/10101* (2013.01); *G06T 2207/20084* (2013.01); *G06T 2207/30041* (2013.01)

(56) References Cited

U.S. PATENT DOCUMENTS

| | | | |
|---|---|---|---|
| 9,779,492 B1* | 10/2017 | Garnavi | G06T 7/0002 |
| 9,824,189 B2* | 11/2017 | Sawada | G06F 19/3418 |
| 9,953,425 B2* | 4/2018 | Lin | G06K 9/627 |
| 2005/0283450 A1* | 12/2005 | Matsugu | G06K 9/00604 706/20 |
| 2006/0204053 A1* | 9/2006 | Mori | G06K 9/00 382/118 |
| 2010/0277691 A1 | 11/2010 | Huang et al. | |
| 2012/0184845 A1* | 7/2012 | Ishikawa | A61B 3/102 600/425 |
| 2015/0201829 A1* | 7/2015 | Yang | G01N 21/4795 382/131 |
| 2016/0100806 A1 | 4/2016 | Mwanza et al. | |
| 2016/0117587 A1* | 4/2016 | Yan | G06N 3/08 706/20 |

OTHER PUBLICATIONS

Schlegl, Thomas, et al. "Automatic segmentation and classification of intraretinal cystoid fluid and subretinal fluid in 3d-oct using convolutional neural networks." Investigative Ophthalmology & Visual Science 56.7 (2015): 5920-5920.*
Shah A, Abramoff MD, Wu X. Simultaneous Multiple Surface Segmentation Using Deep Learning. InDeep Learning in Medical Image Analysis and Multimodal Learning for Clinical Decision Support Sep. 14, 2017 (pp. 3-11). Springer, Cham.*
Cireşan, Dan, Ueli Meier, and Jürgen Schmidhuber. "Multi-column deep neural networks for image classification." arXiv preprint arXiv:1202.2745 (2012).*
K. McDonough, I. Kolmanovsky and I. V. Glybina, "A neural network approach to retinal layer boundary identification from optical coherence tomography images," 2015 IEEE Conference on Computational Intelligence in Bioinformatics and Computational Biology (CIBCB), Niagara Falls, ON, 2015, pp. 1-8. (Year: 2015).*
Yan, Z., Zhang, H., Piramuthu, R., Jagadeesh, V., DeCoste, D., Di, W., & Yu, Y. (2015). HD-CNN: hierarchical deep convolutional neural networks for large scale visual recognition. In Proceedings of the IEEE international conference on computer vision (pp. 2740-2748). (Year: 2015).*
Jiu et al, Human body part estimation from depth images viaspatially-constrained deep learning, Pattern Recognition Letters 50 (2014) 122-129 (Year: 2014).*
Xu, Yan, et al. "Deep learning of feature representation with multiple instance learning for medical image analysis." 2014 IEEE international conference on acoustics, speech and signal processing (ICASSP). IEEE, 2014. (Year: 2014).*
Lu, Xin, et al. "Deep multi-patch aggregation network for image style, aesthetics, and quality estimation." Proceedings of the IEEE International Conference on Computer Vision. 2015. (Year: 2015).*
Lessmann et al, "Deep convolutional neural networks for automatic coronary calcium scoring in a screening study with low-dose chest CT," Proc. SPIE 9785, Medical Imaging 2016: Computer-Aided Diagnosis, 978511 (Mar. 24, 2016); doi: 10.1117/12.2216978 (Year: 2016).*
Pradhan, S. et al., "Shallow Semantic Parsing using Support Vector Machines" In Proceedings of the Human Language Technology Conference (HLT/NAACL 2004), May 2, 2004, Boston, MA, USA, 9 pages.
Garvin, M. et al., "Automated 3-D Intraretinal Layer Segmentation of Macular Spectral-Domain Optical Coherence Tomography Images", IEEE Trans Med Imaging, Sep. 28, 2009, 32 pages.
Ciresan, D. et al., "Multi-column Deep Neural Networks for Image Classification", In Proceedings of the 2012 IEEE Conference on Computer Vision and Pattern Recognition (CVPR), Jun. 16, 2012, Providence, RI, USA, 8 pages.
Krizhevsky, A. et al., "ImageNet Classification with Deep Convolutional Neural Networks", In Proceedings of the Twenty-Sixth Annual Conference on Neural Information Processing Systems (NIPS), Dec. 3, 2012, Lake Tahoe, USA, 9 pages.
Gonzalez, A. et al., "Automatic Cyst Detection in OCT Retinal Images Combining Region Flooding and Texture Analysis", In Proceedings of the 2013 IEEE 26th International Symposium on Computer-Based Medical Systems (CBMS), Jun. 20, 2013, Porto, Portugal, 4 pages.
Schlegl, T. et al., "Unsupervised Pre-training Across Image Domains Improves Lung Tissue Classification" Medical Computer Vision: Algorithims for Big Data, Dec. 10, 2014, 12 pages.
ISA European Patent Office, International Search Report and Written Opinion Issued in PCT Application No. PCT/EP2016/054249, May 23, 2016, WIPO, 15 pages.
European Patent Office, Office Action Issued in Application No. 16706882.4, May 14, 2019, Germany, 5 pages.
ISA European Patent Office, International Search Report and Written Opinion Issued in PCT Application No. PCT/EP2016/059877, Jul. 27, 2016, WIPO, 13 pages.
Burgansky-Eliash, Z. et al., "Optical Coherence Tomography Machine Learning Classifiers for Glaucoma Detection: A Preliminary Study," In Journal of Investigative Opthalmology & Visual Science, vol. 46, No. 11, Nov. 2005, 6 pages.
Cox, D.R. et al., "Analysis of Survival Data," CRC Press, vol. 21, Jun. 1, 1984, 18 pages.
Zou, H. et al., "Regularization and variable selection via the elastic net," Statistical Methodology, vol. 67, Issue 2, Mar. 9, 2005, 20 pages.
Myronenko, A. et al., "Point Set Registration: Coherent Point Drift," IEEE Transactions on Pattern Analysis and Machine Intelligence, vol. 32, Issue 12, Mar. 18, 2010, 14 pages.
Montuoro, A. et al., "Motion Artefact Correction in Retinal Optical Coherence Tomography using Local Symmetry," Medical Image Computing and Computer-Assisted Intervention—MICCAI 2014: 17th International Conference, Sep. 14, 2014, Boston, MA, USA, 8 pages.
Sadeghi, N. et al., "Subject-specific prediction using nonlinear population modeling: Application to early brain maturation from DTI," Medical Image Computing and Computer-Assisted Intervention— MICCAI 2014: 17th International Conference, Sep. 14, 2014, Boston, MA, USA, 8 pages.
Wu, J, et al., "Stable registration of pathological 3D-OCT scans using retinal vessels," Ophthalmic Medical Image Analysis First International Workshop, OMIA 2014, Held in Conjunction with MICCAI 2014, At MIT, Sep. 14, 2014, Boston, MA, USA, 10 pages.
Wu, J. et al., "Automated Retinal Fovea Type Distinction in Spectral-domain Optical Coherence Tomography of Retinal vein Occlusion," SPIE 9413, Medical Imaging 2015: Image Processing, Mar. 20, 2015, 8 pages.
European Patent Office, Office Action Issued in Application No. 16720819.8, Oct. 9, 2019, Germany, 4 pages.

* cited by examiner

(a) raw image
(b) IRC (ground truth annotation)
(c) SRF (ground truth annotation)
(d) IRC (prediction)
(e) SRF (prediction)

COMPUTERIZED DEVICE AND METHOD FOR PROCESSING IMAGE DATA

FIELD OF THE INVENTION

The present invention relates to a computerized device and to a method for processing image data. The technical field of the present invention is the processing of image data, like medical image data. For example, said medical image data may be optical coherence tomography data provided by an optical coherence tomography scanner (OCT scanner).

BACKGROUND

In particular, a key driver for vision loss in retinal diseases such as neovascular age-related macular degeneration is the accumulation of retinal edema or fluid. Out of the two components of retinal edema, intraretinal cystoid fluid (IRC) leads to severe vision loss. Conversely, recent evidence suggests that subretinal fluid (SRF) may be associated with better visual acuity. A precise classification and quantification of IRC and SRF may be of great importance for disease management. Similarly, a wide spectrum of other quantifiable morphologic objects may be present in the retina, which may be relevant for visual function, diagnosis or disease management.

A conventional method for processing optical coherence tomography data for automatic cyst detection is described in reference [1]. But, the method described in reference [1] has disadvantages in the calculating speed and in the necessary accuracy.

Accordingly, it is an aspect of the present invention to improve the processing of image data, like optical coherence tomography data.

BRIEF SUMMARY OF THE INVENTION

According to a first aspect, a computerized device for processing image data is proposed. The computerized device comprises a receiving unit which is configured to receive optical coherence tomography data of a tissue, in particular of a human or animal tissue, for example of a retina, a providing unit which is configured to provide a convolutional neural network for processing the optical coherence tomography data, and a processing unit which is configured to process the received optical coherence tomography data using the convolutional neural network for identifying at least one certain object in the tissue. The tissue may be a human or animal tissue, for example a retina.

The at least one certain object identified in the retina, by processing said optical coherence tomography data using the convolutional neural network may include intraretinal cystoid fluid (IRC) and subretinal fluid (SRF).

The processing unit is configured to process the received optical coherence tomography data using the convolutional neural network for outputting resulting image data. Said resulting image data may include the received optical coherence tomography data, wherein the at least one identified object is identified and/or marked in said optical coherence tomography data. For example, the resulting image data may include the optical coherence tomography data, intraretinal cystoid fluids (IRC) (in particular including their positions and volumes) and subretinal fluids (SRF) (in particular including their positions and locations).

By processing the optical coherence tomography data by means of said convolutional neural network, the present computerized device provides the beneficial technical effect of calculating said resulting image data faster and with a higher accuracy.

In particular, the optical coherence tomography data are provided by an optical coherence tomography scanner (OCT scanner) which is capable to scan a retina of a human being or an animal.

The computerized device may be a computer or an embedded system, for example. The embedded system may be part of a scanner or may be coupled with that.

In particular, the convolutional neural network (CNN) is a hierarchically structured feed-forward neural network having one or more pairs of convolutional layers and succeeding max-pooling layers (see references [2] and [3]).

In an embodiment, the processing unit is configured to localize the certain object in the optical coherence tomography data.

The locations of the certain objects in the optical coherence tomography data may be part of the resulting image data. For example, in the resulting image data, the certain objects are marked in the optical coherence tomography data, e.g., by a certain color.

In a further embodiment, the processing unit is configured to quantify a volume of the certain object in the optical coherence tomography data.

The quantities of the certain objects in the optical coherence tomography data may be part of the resulting image data.

In a further embodiment, the processing unit is configured to process the received optical coherence tomography data using the convolutional neural network for identifying intraretinal cystoid fluid and subretinal fluid in the received optical coherence tomography data.

In a further embodiment, the processing unit is configured to segment and to classify the intraretinal cystoid fluid and the subretinal fluid in the received optical coherence tomography data.

In particular, the processing unit is configured to automatically and highly accurately segment and discriminate between normal retinal tissue, intraretinal cystoid fluid and subretinal fluid in retinal optical coherence tomography data. This may enable precise structure-function correlations based on optical coherence tomography data on large scale. In this regard, the processing unit uses said convolutional neural network to capture characteristic visual appearance patterns and classify normal retinal tissue, intraretinal cystoid fluid and subretinal fluid. In particular, the convolutional neural network may be trained by the providing unit in a supervised manner. In an experiment, the applicant trained the convolutional neural network using approximately 300,000 two-dimensional image patches extracted from 157 optical coherence tomography image volumes. In this experiment, all image patches were sampled at random positions. 73.43% of the patches show healthy tissue, 8.63% show IRC and 17.94% show SRF. Details for that are described in the following.

In a further embodiment, the processing unit is configured to localize each of the intraretinal cystoid fluid regions and to localize each of the subretinal fluid regions in the optical coherence tomography data.

In particular, localization information for the locations of the intraretinal cystoid fluid and further localization information for the locations of the subretinal fluid may be incorporated to the resulting image data.

In a further embodiment, the processing unit is configured to quantify a volume of each of the intraretinal cystoid fluid regions and to quantify a volume of each of the subretinal fluid regions in the optical coherence tomography data.

In particular, a quantity or volume of each of the intraretinal cystoid fluid regions and a further quantity or a further volume of each of the subretinal fluid regions may be incorporated into the resulting image data.

In a further embodiment, the optical coherence tomography data are spectral-domain optical coherence tomography images.

In a further embodiment, the providing unit is configured to provide the convolutional neural network with a number of layer stacks, wherein each of the layer stacks includes one or more pairs of convolutional layers and max-pooling layers, one or more fully-connected layers and a terminal classification layer.

In more detail, in the convolutional neural network (CNN), a stack of convolution and max-pooling layer pairs may be followed by one or more fully-connected layers and a terminal classification layer. In particular, a plurality of stacks of pairs of convolution and max-pooling layers may be fed into the first fully-connected layer of the convolutional neural network. As a result, it is enabled to train the convolutional neural network based on multiple scales. Further, the processing unit may be adapted to use the convolutional neural network to perform voxel-wise classification on visual inputs and corresponding quantitative spatial location information.

Furthermore, by using said max-pooling layers in the convolutional neural network used by the present computerized device, the outputs of the max-pooling layers get smaller. Thus, the necessary memory space is advantageously reduced.

In a further embodiment, the providing unit is configured to train the convolutional neural network using a plurality of two-dimensional image patches and/or a plurality of three-dimensional image patches extracted from a plurality of spectral-domain optical coherence tomography images.

In a further embodiment, the receiving unit is configured to provide the convolutional neural network (CNN), in particular the terminal classification layer, with at least one location information of the two-dimensional image patches or the three-dimensional image patches.

By providing said location information to the terminal classification layer, the accuracy of the processing unit is further enhanced.

In a further embodiment, the receiving unit is configured to provide the convolutional neural network (CNN), in particular the terminal classification layer, with Euclidean distances of patch centers of the two-dimensional image patches and/or three-dimensional image patches and three-dimensional coordinates of the patch centers.

In particular, besides the visional appearance of the image patches, the convolutional neural network may be provided with the Euclidean distances of the patch centers to the fovea and the three-dimensional coordinates of the patch centers. Therefore, the accuracy of the processing unit is further enhanced advantageously. Moreover, based on the image patches of the training set, the convolutional neural network may learn representative and discriminative features appropriate for pixel-wise image classification of the optical coherence tomography data. The pixel-wise classification may result in a segmentation of the whole optical coherence tomography volume into normal retinal tissue, intraretinal cystoid fluid and subretinal fluid.

In a further embodiment, the plurality of layer stacks uses different image patches of different sizes.

In a further embodiment, the different two-dimensional image patches are centered at a same position.

The respective unit, e.g. the providing unit or the processing unit, may be implemented in hardware and/or in software. If said unit is implemented in hardware, it may be embodied as a device, e.g. as a computer or as a processor or as a part of a system, e.g. a computer system. If said unit is implemented in software it may be embodied as a computer program product, as a function, as a routine, as a program code or as an executable object.

Any embodiment of the first aspect may be combined with any embodiment of the first aspect to obtain another embodiment of the first aspect.

According to a second aspect, a method for processing image data is proposed. The method includes a step of receiving optical coherence tomography data of a tissue, in particular of a retina, a step of providing a convolutional neural network for processing the optical coherence tomography data, and a step of processing the received optical coherence tomography data using the convolutional neural network for identifying at least one certain object in the tissue.

According to a third aspect, the invention relates to a computer program comprising a program code for executing the method of the second aspect for processing image data when run on at least one computer.

In the following, exemplary embodiments of the present invention are described with reference to the enclosed figures.

BRIEF DESCRIPTION OF THE DRAWINGS

Similar or functionally similar elements in the figures have been allocated the same reference signs if not otherwise indicated.

DETAILED DESCRIPTION OF THE EMBODIMENTS

Figure 1:
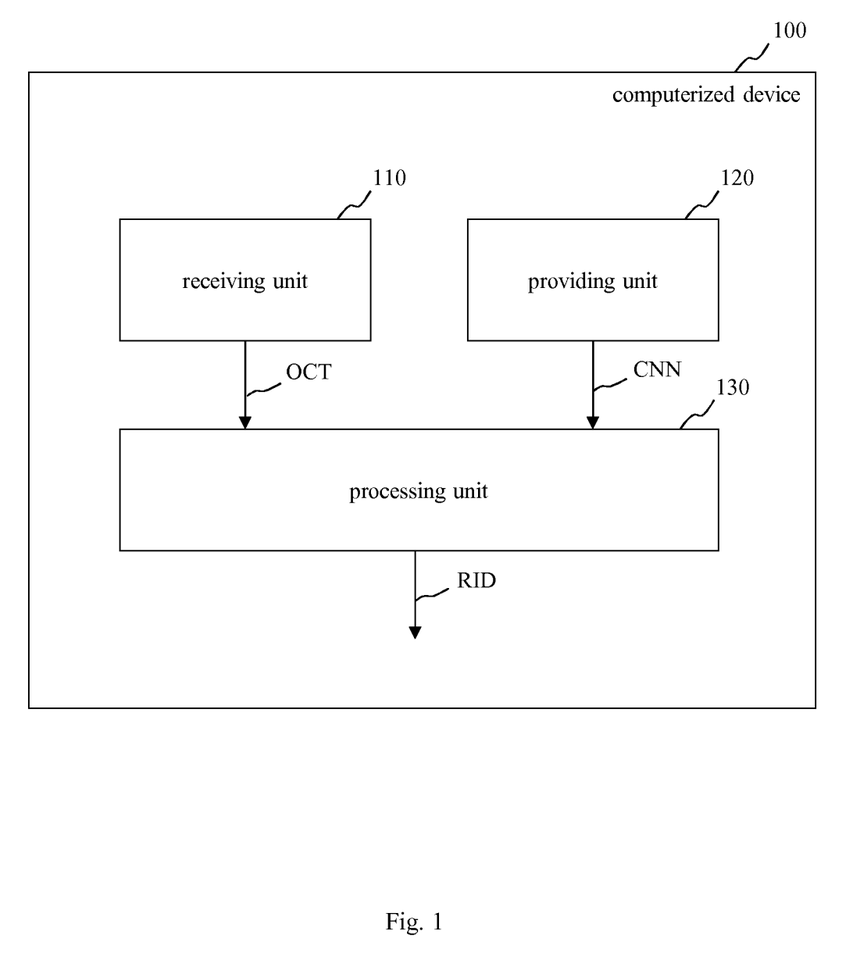
FIG. 1 shows a schematic block diagram of an embodiment of a computerized device for processing image data.

In FIG. 1, a schematic block diagram of an embodiment of a computerized device 100 for processing image data, in particular optical coherence tomography data OCT of a tissue, e.g. of a retina or of a skin, is depicted. Moreover, FIG. 2 shows a schematic block diagram of a system including the computerized device 100 of FIG. 1, an OCT scanner 200 for providing the optical coherence tomography data OCT and a display 300 for displaying a result calculated by the computerized device 100.

Figure 2:
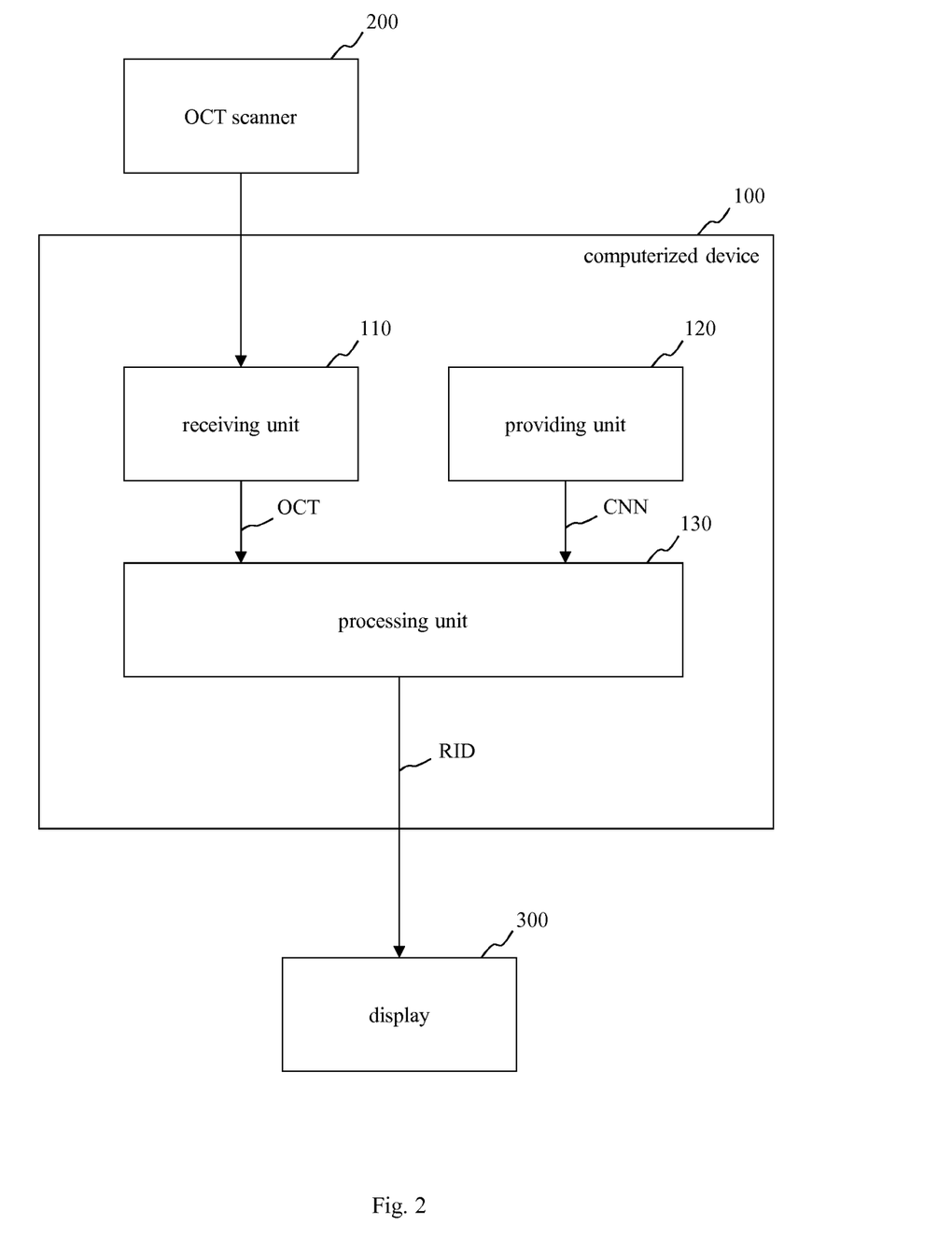
FIG. 2 shows a schematic block diagram of a system including the computerized device of FIG. 1, an optical coherence tomography scanner and a display.

The computerized device 100 of FIG. 1 and FIG. 2 includes a receiving unit 110, a providing unit 120 and a processing unit 130. For example, the computerized device 100 of FIG. 1 is embodied as a computer or as an embedded system.

The receiving unit 110 is configured to receive optical coherence tomography data OCT.

For example, the optical coherence tomography data OCT are spectral-domain optical coherence tomography images.

The providing unit 120 is configured to provide a convolutional neural network CNN for processing the optical coherence tomography data OCT. Examples for such a convolutional neural network CNN are given in FIG. 4 and FIG. 5.

The processing unit 130 is configured to process the received optical coherence tomography data OCT using the convolutional neural network CNN for identifying at least one certain object IRC, SRF in the retina. For example, the object may be a fluid object. In particular, the object is an intraretinal cystoid fluid IRC or a subretinal fluid SRF.

Figure 3:
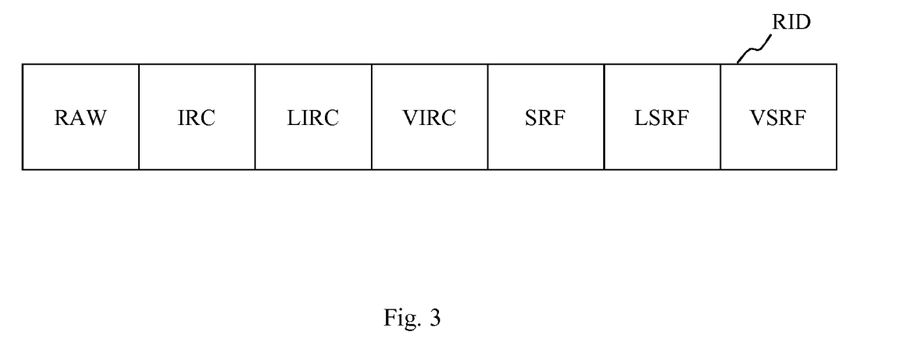
FIG. 3 shows a schematic block diagram of resulting image data provided by the computerized device of FIG. 1 or FIG. 2.

As a result of processing the received optical coherence tomography data OCT by using the convolutional neural network CNN, the processing unit 130 may output resulting image data RID (see FIG. 3).

In particular, the providing unit 120 is configured to compute the convolutional neural network CNN based on training data. Moreover, the processing unit 130 may have the same architecture as the providing unit 120 and may use the convolutional neural network CNN trained by the providing unit 120.

In particular, the processing unit 130 is configured to localize the certain object IRC, SRF in the optical coherence tomography data OCT.

Additionally or alternatively, the processing unit 130 may be configured to quantify a volume VIRC, VSRF of the certain object IRC, SRF in the optical coherence tomography data OCT.

In particular, for the above mentioned example, that the objects may include intraretinal cystoid fluid IRC and subretinal fluid SRF, the processing unit 130 may be configured to process the received optical coherence tomography data OCT using the convolutional neural network CNN for identifying intraretinal cystoid fluid IRC and subretinal fluid SRF in the received optical coherence tomography data OCT. In this regard, the processing unit 130 may be configured to segment and to classify the intraretinal cystoid fluid IRC and the subretinal fluid SRF in the received optical coherence tomography data OCT.

In particular, the processing unit 130 may localize each of the intraretinal cystoid fluid regions IRC and each of the subretinal fluid regions SRF in the optical coherence tomography data OCT.

Figure 6:
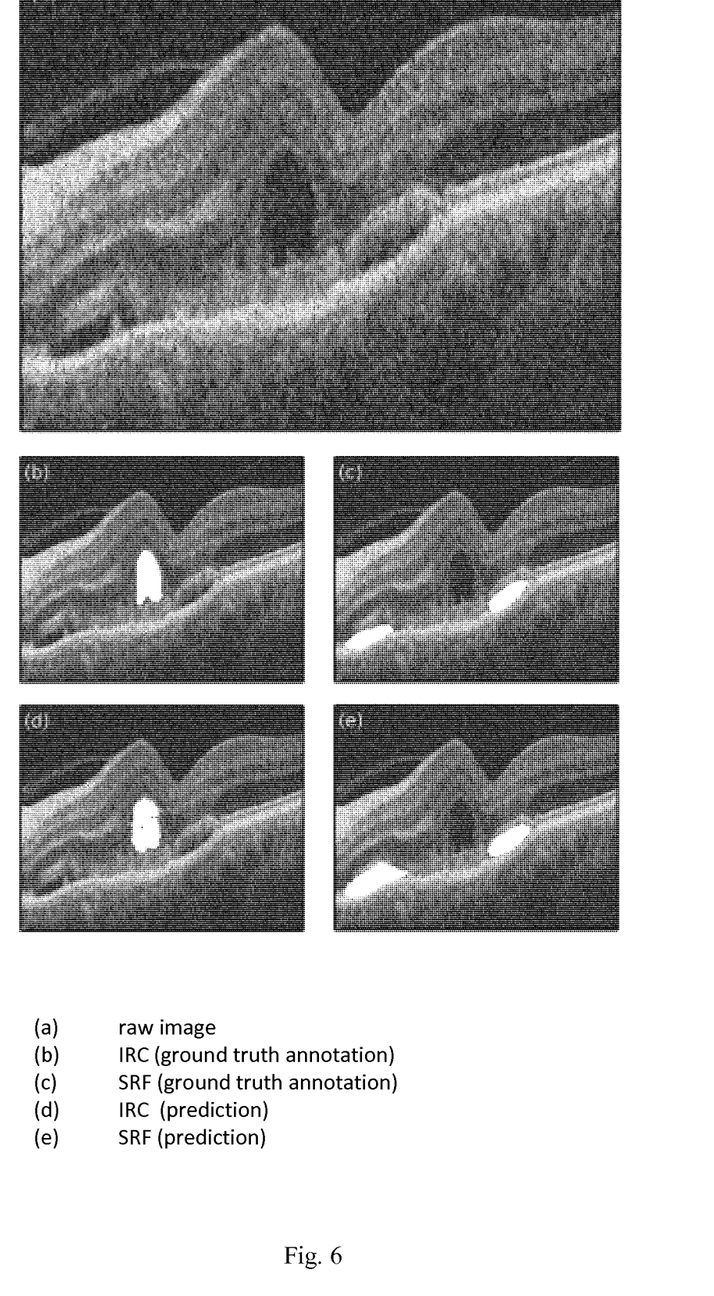
FIG. 6 shows different views of optical coherence tomography data.

In this connection, FIG. 3 shows a schematic block diagram of such resulting image data RID provided by the computerized device 100 of FIG. 1. It may be mentioned, that FIG. 3 schematically shows different information contents of said resulting image data RID. Examples for actual images and, therefore, actual resulting image data RID are shown in FIG. 6.

For example, said resulting image data RID of FIG. 3 may include the raw data RAW, exemplarily corresponding to the received optical coherence tomography data OCT, identified intraretinal cystoid fluids IRC, determined locations LIRC of the identified intraretinal cystoid fluids IRC, determined volumes VIRC of the identified intraretinal cystoid fluids IRC, identified subretinal fluids SRF, determined locations LSRF of the identified subretinal fluids SRF, and determined volumes VSRF of the identified subretinal fluids SRF.

Moreover, the providing unit 120 of FIG. 1 and FIG. 2 may be configured to provide the convolutional neural network CNN with a number of layer stacks S1, S2, wherein each of the layer stacks S1, S2 includes one or more pairs P11, P12, P13, P21, P22 (see FIG. 4 and FIG. 5) of convolutional layers CONV1-CONV3 and max-pooling layers MP1-MP3, one or more fully-connected layers FC1, FC2 and a terminal classification layer CL.

Figure 4:
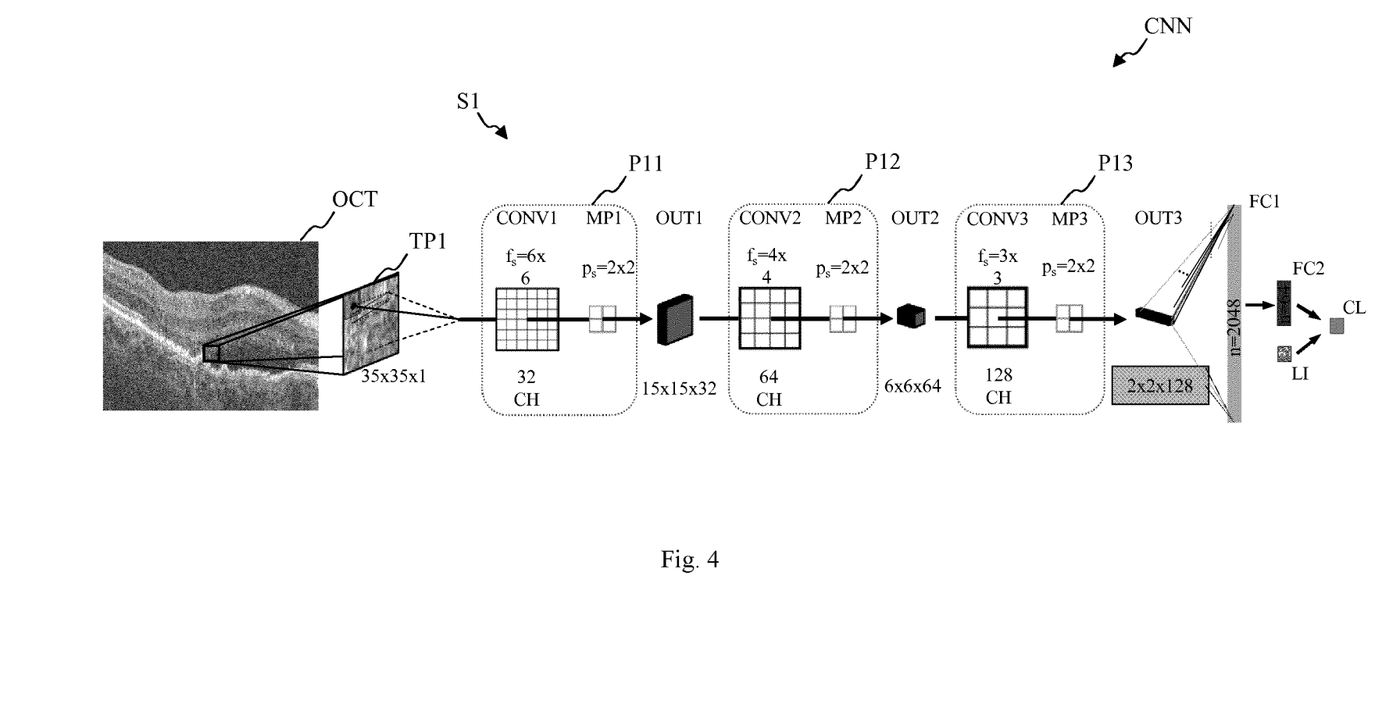
FIG. 4 shows a schematic view of a first embodiment of a convolutional neural network useable by the computerized device of FIG. 1 or FIG. 2.
Figure 5:
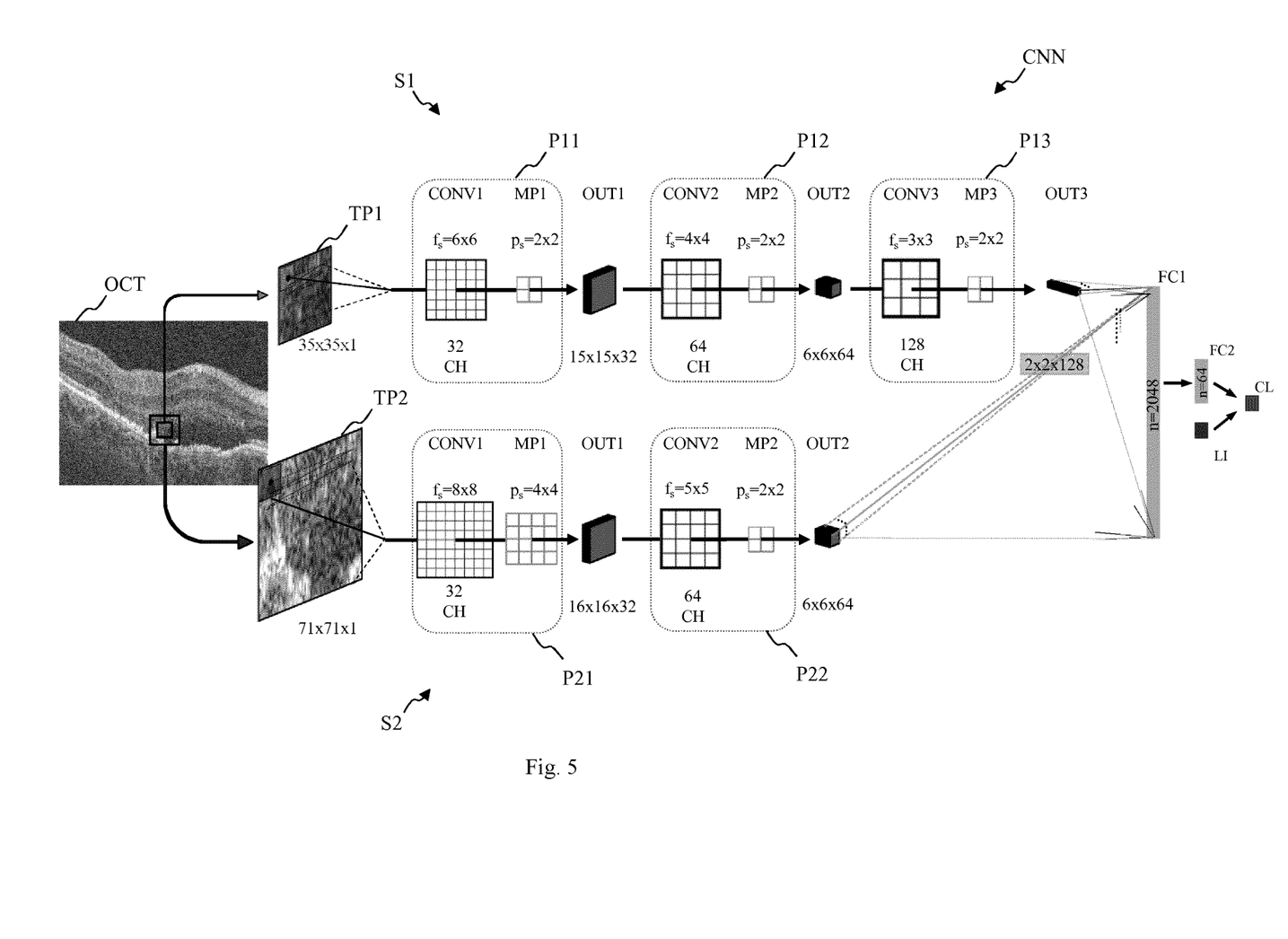
FIG. 5 shows a schematic view of a second embodiment of a convolutional neural network useable by the computerized device of FIG. 1 or FIG. 2.

In this regard, FIG. 4 and FIG. 5 show different embodiments of such a convolutional neural network CNN that may be used by the computerized device 100.

In FIG. 4, a schematic view of a first embodiment of a convolutional neural network CNN that may be used by the computerized device 100 of FIG. 1 is depicted.

The convolutional neural network CNN of FIG. 4 may be trained by a plurality of two-dimensional image patches TP1 extracted from a number of spectral-domain optical coherence tomography images OCT. As shown on the left side of FIG. 4, the respective two-dimensional image patch TP1 is extracted from said spectral-domain optical coherence tomography image OCT and input into a layer stack S1 of the convolutional neural network CNN. The layer stack S1 of FIG. 4 has three pairs P11, P12 and P13 of convolutional layers CONV1-CONV3 and respectively succeeding max-pooling layers MP1-MP3.

As shown in FIG. 4, the two-dimensional image patch TP1 has a size of 35×35. Further, as shown in FIG. 4, the resulting outputs OUTk of the k pairs of convolutional layer CONVk and max-pooling layer MPk are the inputs of the succeeding layers (with $k \in [1, 2, 3]$), with corresponding convolution filter sizes $f_s$ and sizes of the pooling region $p_s$.

The output OUT3 of the layer stack S1 including said three pairs P11, P12 and P13 is input to a first fully-connected layer FC1. The output of the first fully-connected layer FC1 is input to the second fully-connected layer FC2.

The succeeding terminal classification layer CL has as inputs the output of the second fully-connected layer FC2 and location information LI of the two-dimensional image patches TP1. Said location information LI may include Euclidean distances of the patch centers of the two-dimensional image patches TP1, for example in relation to the fovea or the retinal surface, and three-dimensional coordinates of the patch centers of the two-dimensional image patches TP1.

FIG. 5 shows a schematic view of a second embodiment of a convolutional neural network CNN which may be used by the computerized device 100 of FIG. 1.

In contrast to the embodiment of FIG. 4, the convolutional neural network CNN of FIG. 5 includes two different layer stacks S1 and S2. The layer stack S1 uses first two-dimensional image patches TP1 extracted from the optical coherence tomography data OCT. For example, said first two-dimensional image patches TP1 have a size of 35×35, respectively.

The second layer stack S2 uses second two-dimensional image patches TP2 having a size of 71×71. In particular, the different two-dimensional image patches TP1 and TP2 have different sizes, here 35×35 and 71×71, but are centered at the same position, respectively.

As shown in FIG. 5, the outputs of both layer stacks S1, S2 are connected densely with all neurons of the first fully-connected layer FC1. As in FIG. 4, the location information LI are fed jointly with the activations of the second fully-connected layer FC2 in to the classification layer CL.

In the following, more details for the CNNs of FIG. 4 and FIG. 5 are described:

For example, the optical coherence tomography data OCT comprises M tuples of medical imaging data, corresponding clinical reports and voxel-wise ground-truth class labels $\langle I^m; T^m; L^m \rangle$, with m=1, 2, . . . , M, where $I^m \in \mathbb{R}^{n \times n}$ is an intensity image (e.g., a slice of an SD-OCT volume scan of the retina) of size n×n, $L^m \in \{1, \ldots, K+1\}^{n \times n}$ is an array of the same size containing the corresponding ground-truth class labels and $T^m$ is the corresponding textual report. During training by the providing unit 120, $\langle I^m; T^m \rangle$ is given. The providing unit 120 trains the CNN such that it predicts $L^m$ from on new testing data. The voxel-level ground-truth class labels $L^m$ may be not used for training, but only for evaluation of the voxel-wise prediction accuracy.

To capture visual information at different levels of detail, the small square-shaped image patches $\dot{x}_i^m \in \mathbb{R}^{\alpha \times \alpha}$ of size α and larger square-shaped image patches $\ddot{x}_i^m \in \mathbb{R}^{\beta \times \beta}$ of size β are extracted with α<β<n centered at the same spatial position $c_i^m$ from volume $I^m$, where i is the index of the centroid of the image patches TP1, TP2.

For each image patch TP1, TP2, two additional quantitative location parameters are provide to the CNN: (i) the 3D spatial coordinates $c_i^m \in \Omega \subset \mathbb{R}^3$ of the centroid i of the image patches and (ii) the Euclidean distance $d_i^m \in \Omega \subset \mathbb{R}$ of the patch center i to a given reference structure (e.g.: fovea) within the volume.

Moreover, objects (e.g. pathology) may be assumed that are reported together with a textual description of their approximate spatial location. Thus, a report $T^m$ consists of K pairs of text snippets $\langle t^{m,k}{}_P, t^{m,k}{}_{Loc} \rangle$, with k=1, 2, . . . , K, where $t^{m,k}{}_P \in P$ describes the occurrence of a specific object class term and $t^{m,k}{}_{Loc} \in L$ represents the semantic description of its spatial locations. These spatial locations can be both abstract subregions (e.g., centrally located) of the volume or concrete anatomical structures. Note that $t^{m,k}{}_{Loc}$ does not contain quantitative values, and the link between these descriptions and image coordinate information may be not known. This semantic information can come in Γ orthogonal semantic groups (e.g., in (1) the lowest layer and (2) close to the fovea). That is, different groups represent different location concepts found in clinical reports. The extraction of these pairs from the textual document is based on semantic parsing (see reference [4]). The textual report $T^m$ may be decomposed into the corresponding semantic target label $s^m \in \{0,1\}^{K \Sigma_\gamma n_\gamma}$, with γ=1, 2, . . . , Γ, where K is the number of different object classes which should be classified (e.g. cyst), and $n_\gamma$ is the number of nominal region classes in one semantic group γ of descriptions (e.g., $n_\gamma=3$ for upper vs. central vs. lower layer, $n_\gamma=2$ for close vs. far from reference structure).

I.e., if there are two groups, then $s^m$ is a K-fold concatenation of pairs of a binary layer group $g^k{}_1 \in \{0,1\}^{n_1}$ with $n_1$ bits representing different layer classes and a binary reference location group $g^k{}_2 \in \{0,1\}^{n_2}$ with $n_2$ bits representing relative locations to a reference structure. For all object classes, all bits of the layer group, and all bits of the reference location group are set to 1, if they are mentioned mutually with the respective object class in the textual report. All bits of the corresponding layer group and all bits of the corresponding reference location group are set to 0, where the respective object class is not mentioned in the report. The vector $s^m$ of semantic target labels is assigned to all input tuples $\langle \dot{x}_i^m, \ddot{x}_i^m, c_i^m, d_i^m \rangle$ extracted from the corresponding volume $I^m$.

FIG. 6 shows different views of optical coherence tomography data. In detail, FIG. 6 (*a*) shows an intensity image of a single slice (zx-view) of a clinical SD-OCT scan (RAW) of the retina. FIG. 6 (*b*) shows a voxel-wise ground-truth annotations of cysts (IRCs). FIG. 6 (*c*) shows a voxel-wise ground-truth annotations of SRFs. FIG. 6 (*d*) shows predictions for cysts (LIRC), and FIG. 6 (*e*) shows predictions for SRFs (LSRF).

For evaluating the present CNN, 157 clinical high resolution SD-OCT volumes of the retina with resolutions of 1024×512×128 voxels were used. From these volumes, pairs of 2D image patches were extracted with scales 35×35 and 71×71 for 300,000 positions. The positions of the patch centers within an image slice as well as the slice number within a volume are sampled randomly. The intensity values of the image patches are normalized by transforming the data to zero-mean and unit variance.

The human retina can be subdivided into different layers. An implementation of an automatic layer segmentation algorithm was used following reference [5]. Based on the top and bottom layer, a retina mask was computed. The voxel positions within this mask are normalized into the range [0, 1], where the voxels at the top and bottom layer (z-axis), the voxels in the first and last column of the image (x-axis) and the voxels in the first and last slice of the volume (y-axis) are assigned to the marginals 0 and 1, respectively. These normalized 3D coordinates are used as location specific inputs.

In every SD-OCT volume, the position of the fovea is also annotated. The annotated position of the fovea is used as reference structure and the Euclidean distance of every image patch center is provided as additional location specific input.

For the purposes of evaluation of voxel-wise classification performance, it is assigned the class label of the patch center extracted from the corresponding volume with voxel-wise annotations to the whole image patch. As already indicated above, 73.43% of the patches are labeled as healthy tissue, 8.63% are labeled as IRC and 17.94% are labeled as SRF. Pairs of patches sampled at different positions within the same volume may partially overlap. The image patches are split on a patient basis into training and test set to perform 4-fold cross-validation, so that there is no patient both in the training, and the test set.

For every approach training of the CNN is performed for 200 epochs. A multi-scale CNN architecture with two parallel stacks of pairs of convolution and max-pooling layers was used (as shown in FIG. 5). These stacks take as input image patches of size 35×35 and 71×71 and comprise three and two pairs of convolution and max-pooling layers respectively (see FIG. 5). The outputs of the max-pooling layers on top of both stacks are concatenated and fed into a fully-connected layer with 2048 neurons. This layer is followed by a second fully-connected layer with 64 neurons. The activations of this layer are concatenated with the spatial location parameters of the patch centers and fed into the terminal classification layer. All layer parameters are learned during classifier training. The architecture of the multi-scale CNN and the detailed model parameters are shown in FIG. 5. The model parameters are found empirically due to preceding experiments. Examples for such experiments are the following:

Experiment (1):

The naive weakly supervised learning approach represents the most restricted learning approach and serves as reference scenario. Classification results are shown in Table 1(a) below. This approach yields a classification accuracy over all three classes of 66.30%. Only 21.94% of samples showing IRC are classified correctly, while the SRF class is classified relatively accurately (90.30% of all patches showing SRF are correctly classified).

Experiment (2):

The classification results of our proposed weakly supervised learning approach using semantic descriptions are shown in Table 1(b). This approach yields a classification accuracy over all three classes of 81.73% with lower accuracy for the healthy class (78.72%) compared to the SRF class (92.09% accuracy) which is also the best performance on the SRF class over all three approaches.

Experiment (3):

As expected, the supervised learning approach performs best. This approach yields an overall classification accuracy over all three classes of 95.98%. Classification results are shown in Table 1(c). While it has most difficulties with IRC (89.61% accuracy) it still obtains the highest accuracy for IRC over all three approaches. This approach also performs best for the healthy class (97.70% accuracy).

As indicated above, the below Table 1 shows a confusion matrix of classification results and corresponding class-wise accuracies on (a) the naive weakly supervised learning approach, (b) the weakly supervised learning approach using semantic descriptions and (c) the supervised learning approach.

TABLE 1

| | | prediction | | | |
|---|---|---|---|---|---|
| | | healthy | IRC | SRF | accuracy |
| (a) | healthy | 144329 | 4587 | 70994 | 0.6563 |
| | IRC | 10391 | 5653 | 9718 | 0.2194 |
| | SRF | 4978 | 231 | 48511 | 0.9030 |
| (b) | healthy | 173121 | 10603 | 36186 | 0.7872 |
| | IRC | 2230 | 22102 | 1430 | 0.8579 |
| | SRF | 2963 | 1285 | 49472 | 0.9209 |
| (c) | healthy | 214848 | 2303 | 2759 | 0.9770 |
| | IRC | 2222 | 23086 | 454 | 0.8961 |
| | SRF | 3670 | 638 | 49412 | 0.9198 |

Figure 7:
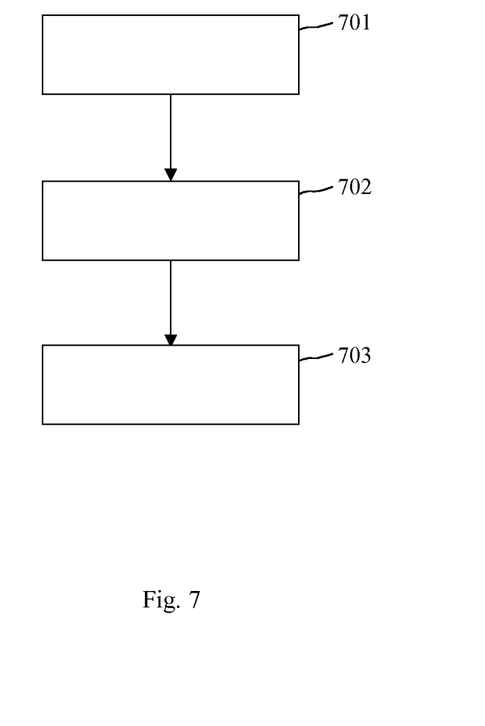
FIG. 7 shows an embodiment of a sequence of method steps for processing image data.

In FIG. 7, a sequence of method steps for processing image data OCT is depicted. The method of FIG. 7 includes the following method steps 701-703:

In step 701, optical coherence tomography data OCT of a tissue, in particular of a human or animal tissue, for example of a retina or of a skin, are received.

In step 702, a convolutional neural network CNN for processing the optical coherence tomography data OCT is provided. Examples for such a convolutional neural network CNN are depicted in FIG. 4 and FIG. 5.

In step 703, the received optical coherence tomography data OCT are processed by using the provided convolutional neural network CNN for identifying at least one certain object in the tissue, in particular of the human or animal tissue, for example of the retina, for example intraretinal cystoid fluids and subretinal fluids, or in the skin.

Computerized devices may be suitably designed for implementing embodiments of the present invention as described herein. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

In particular, each block of the block diagrams may be implemented by one or more computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

More generally, while the present invention has been described with reference to certain embodiments, it will be understood by those skilled in the art that various changes may be made and equivalents may be substituted without departing from the scope of the present invention. In addition, many modifications may be made to adapt a particular situation to the teachings of the present invention without departing from its scope. Therefore, it is intended that the present invention not be limited to the particular embodiments disclosed, but that the present invention will include all embodiments falling within the scope of the appended claims.

REFERENCE NUMERALS 100 computerized device
110 receiving unit
120 providing unit
130 processing unit
200 computer tomography scanner
300 display
701 method step
702 method step
703 method step
CH channel
CL terminal classification layer
CNN convolutional neural network
CONV convolutional layer
FC fully-connected
IRC intraretinal cystoid fluid
LIRC location of intraretinal cystoid fluid
LSRF location of subretinal fluid
MP max-pooling layer
OCT optical coherence tomography data
OUT output
P11 first pair of convolutional layer and max-pooling layer of first layer stack
P12 second pair of convolutional layer and max-pooling layer of first layer stack
P13 third pair of convolutional layer and max-pooling layer of first layer stack
P21 first pair of convolutional layer and max-pooling layer of second layer stack
P22 second pair of convolutional layer and max-pooling layer of second layer stack
RID resulting image data
S1 layer stack
S2 layer stack SRF subretinal fluid
TP1 two-dimensional patch
TP2 two-dimensional patch
VIRC volume of intraretinal cystoid fluid
VSRF volume of subretinal fluid

REFERENCES

[1] Gonzalez, A., Remeseiro, B., Ortega, M., Penedo, M. G., & Charlon, P.: Automatic cyst detection in OCT retinal images combining region flooding and texture analysis. In Computer-Based Medical Systems (2013) 397-400;
[2] Ciresan, D., Meier, U., Schmidhuber, J.: Multi-column deep neural networks for image classication. In: Conference on Computer Vision and Pattern Recognition, IEEE (2012) 3642-3649;
[3] Krizhevsky, A., Sutskever, I., Hinton, G. E.: Imagenet classication with deep convolutional neural networks. In: Advances in Neural Information Processing Systems. Volume 1. (2012) 4;
[4] Pradhan, S., Ward, W., Hacioglu, K., Martin, J., Jurafsky, D.: Shallow semantic parsing using support vector machines. In: Proceedings of HLT/NAACL. (2004) 233;
[5] Garvin, M. K., Abramoff, M. D., Wu, X., Russell, S. R., Burns, T. L., Sonka, M.: Automated 3-D intraretinal layer segmentation of macular spectral-domain optical coherence tomography images. Medical Imaging, IEEE Transactions on 28(9) (2009) 1436-1447

The invention claimed is:

1. A computerized device for processing image data, the computerized device comprising:
one or more processors configured to execute instructions to:
receive optical coherence tomography data of a tissue, in particular of a retina,
provide a convolutional neural network for processing the optical coherence tomography data,
directly process raw image data included within the received optical coherence tomography data using the convolutional neural network for identifying intraretinal cystoid fluid and subretinal fluid in the received optical coherence tomography data, and
provide the convolutional neural network with a plurality of layer stacks, wherein the plurality of layer stacks simultaneously uses different two-dimensional or three-dimensional image patches of different sizes.

2. The computerized device of claim 1,
wherein the one or more processors are further configured to execute instructions to segment and to classify the intraretinal cystoid fluid and the subretinal fluid in the received optical coherence tomography data.

3. The computerized device of claim 2, wherein the intraretinal cystoid fluid and the subretinal fluid are classified at least in part based on a relative position to one or more retinal layers.

4. The computerized device of claim 1,
wherein the one or more processors are further configured to execute instructions to localize each of the intraretinal cystoid fluids and to localize each of the subretinal fluids in the optical coherence tomography data.

5. The computerized device of claim 1,
wherein the one or more processors are further configured to execute instructions to quantify a volume of each of the intraretinal cystoid fluids and to quantify a volume of each of the subretinal fluids in the optical coherence tomography data.

6. The computerized device of claim 1,
wherein the optical coherence tomography data are spectral-domain optical coherence tomography images.

7. The computerized device of claim 1,
wherein each of the layer stacks includes one or more pairs of convolutional layers and max-pooling layers, one or more fully-connected layers and a terminal classification layer.

8. The computerized device of claim 7,
wherein the one or more processors are further configured to execute instructions to train the convolutional neural network using a number of two-dimensional image patches or a number of three-dimensional image patches extracted from a plurality of spectral-domain optical coherence tomography images.

9. The computerized device of claim 8,
wherein the one or more processors are further configured to execute instructions to provide the convolutional neural network, in particular the terminal classification layer, with at least one location information of the two-dimensional or the three-dimensional image patches.

10. The computerized device of claim 8,
wherein the one or more processors are further configured to execute instructions to provide the convolutional neural network, in particular the terminal classification layer, with Euclidean distances of patch centers of the two-dimensional or the three-dimensional image patches and three-dimensional coordinates of the patch centers.

11. The computerized device of claim 8, wherein the convolutional neural network is trained exclusively using image patches extracted from the plurality of spectral-domain optical coherence tomography images.

12. The computerized device of claim 1,
wherein the different two-dimensional or the three-dimensional image patches are centered at a same position.

13. A method for processing image data via a computerized device, the method comprising:
receiving optical coherence tomography data of a tissue, in particular of a retina,
providing a convolutional neural network for processing the optical coherence tomography data,
directly processing raw image data included within the received optical coherence tomography data using the convolutional neural network for identifying intraretinal cystoid fluid and subretinal fluid in the received optical coherence tomography data, and
provide the convolutional neural network with a plurality of layer stacks, wherein the plurality of layer stacks simultaneously uses different two-dimensional or three-dimensional image patches of different sizes.

* * * * *